United States Patent [19]

Reinehr et al.

[11] Patent Number: 5,288,868
[45] Date of Patent: Feb. 22, 1994

[54] PROCESS FOR THE PREPARATION OF 2-HYDROXY-4,6-DIARYL-1,3,5-TRIAZINE

[75] Inventors: Dieter Reinehr, Kandern, Fed. Rep. of Germany; Jean-Pierre Bacher, Buschwiller, France

[73] Assignee: Ciba-Geigy Corporation, Ardsley, N.Y.

[21] Appl. No.: 14,894

[22] Filed: Feb. 8, 1993

[30] Foreign Application Priority Data

Feb. 13, 1992 [CH] Switzerland ............................ 426/92

[51] Int. Cl.$^5$ ........................................... C07D 251/52
[52] U.S. Cl. ................................................... 544/219
[58] Field of Search ......................................... 544/219

[56] References Cited

FOREIGN PATENT DOCUMENTS 1193057 5/1965 Fed. Rep. of Germany .
1049513 11/1966 United Kingdom .

OTHER PUBLICATIONS

Alsofrom et al, J. Het. Chem, vol. 13, pp. 917–919 (1976).
Berichte Der Deutschen Chemischen Gesellschaft 23(13), 2919–2922 (1890).
Journal of the Chemical Society D, Chemical Communications 10, 498–499 (1971).
Journal of Heterocyclic Chemistry 13(4), 917–919 (1976).
Journal of Organic Chemistry 42(14), 2530–2532 (1977).
A. Pinner, Chem. Ber. 23, 2919 (1890).

*Primary Examiner*—John M. Ford
*Attorney, Agent, or Firm*—Kevin T. Mansfield; Edward McC. Roberts

[57] ABSTRACT

There is disclosed a process for the preparation of 2-hydroxy-4,6-diaryl-1,3,5-triazines by reacting an aromatic nitrile with an alkali metal amide and an alkyl haloformate, using an equimolar amount of each, which process is carried out as a one-pot synthesis.

The triazine derivatives obtained by the process of this invention are used as intermediates for the synthesis of UV absorbers.

8 Claims, No Drawings

PROCESS FOR THE PREPARATION OF 2-HYDROXY-4,6-DIARYL-1,3,5-TRIAZINE

The present invention relates to a process for the pirparation of 2-hydroxy-4,6-diaryl-1,3,5-triazines from simple starting materials such as substituted benzonitriles, alkyl chloroformates and sodium amide, which process is carried out as a one-pot synthesis.

Specifically, the invention relates to a process for the preparation of a 2-hydroxy-4,6-diaryl-1,3,5-triazine of formula

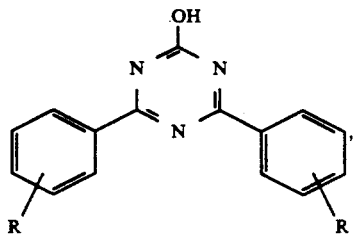

which comprises reacting an aromatic nitrite with an alkyl haloformate and an alkali metal amide, using an equimolar amount of each, in accordance with the reaction scheme

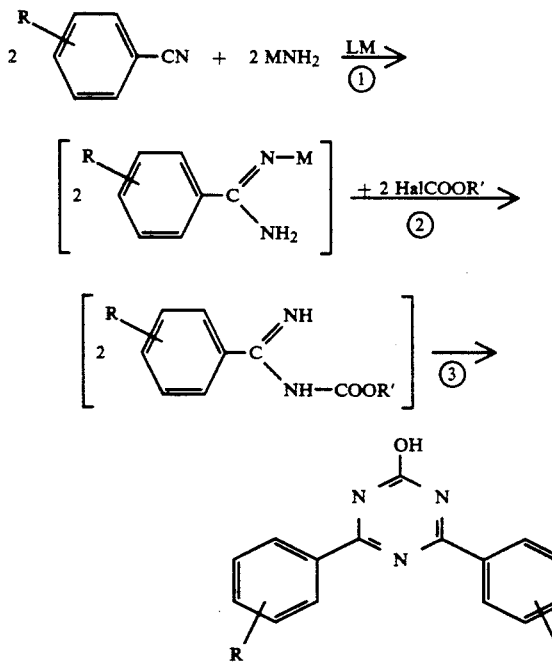

wherein
R is hydrogen, halogen, $C_1$-$C_4$alkyl or $C_1$-$C_4$alkoxy,
R' is $C_1$-$C_4$alkyl
Hal is a halogen atom,
M is an alkali metal, and
LM is an inert organic solvent having a boiling point in the range from 160° to 250° C.

$C_1$-$C_4$Alkyl is typically methyl, ethyl, n-propyl, isopropyl, n-butyl, isobutyl, sec-butyl or tert-butyl; and $C_1$-$C_4$alkoxy is typically methoxy, ethoxy, isopropoxy, isobutoxy or tert-butoxy.

Halogen is fluoro, chloro or bromo, preferably chloro.

Suitable bases for the novel process are lithium, potassium or sodium amide. Sodium amide is preferably used in the form of a 60–70% suspension.

Typical examples of starting aromatic nitriles are benzonitrile, methyl benzonitrile, ethyl benzonitrile, propyl benzonitrile, n-butyl benzonitrile, tert-butyl benzonitrile and chlorobenzonitrile. Preferred starting materials are benzonitrile, 3-methylbenzonittile, 4-methylbenzonitrile, 3-chlorobenzonitrile or 4-chlorobenzonitrile. Benzonitrile is particularly preferred.

Exemplary alkyl haloformates are methyl bromoformate, methyl chloroformate, ethyl bromoformate or ethyl chloroformate. It is preferred to use the last mentioned compound in the process of this invention.

Typical examples of inert organic solvents are o-dichlorobenzene, nitrobenzene, 1,2,3-trimethylbenze, a mixture of 26.5% by weight of diphenyl and 73.5% by weight of diphenyl ether sold by Dow Chemical as ®Dowtherm or anisole. The preferred solvent is a mixture of 26.5% by weight of diphenyl and 73.5% by weight of diphenyl ether.

The reaction of the first step is carried out in the temperature range from 50° to 150° C., preferably from 70° to 120° C., and the reaction of the second step from 5° to 50° C., preferably from 10° to 40° C.; the reaction of the third step is carried out in the temperature range from 120° to 230° C., preferably from 50° to 200° C.

The cyclisation to give the 2-hydroxy-4,6-diaryl-1,3,5-triazine is also conveniently carried out under a reduced pressure of 150 to 200 mbar to effect rapid removal of ethanol and urethane.

The compounds of formula (1) are known, inter alia from A. Pinner, Chem. Ber. 23, 2919 (1890).

Compared with the process described in this reference, the novel compounds of formula (1) are obtained in a one-step process without isolation of the alkyl benzimidoylcarbamate. In addition, the hydroxydiphenyl-1,3,5-triazine of formula (1) is obtained in such good purity that it can be conveniently further processed without isolation.

The triazine compounds obtained by the inventive process are used as intermediates for the synthesis of UV absorbers.

The invention is illustrated by the following non-limitative Examples.

EXAMPLE 1

Preparation of 2-hydroxy-4,6-diphenyl-1,3,5-triazine 100 g (2.4 mol) of sodium amide (95%) are stirred for 12 hours at room temperature in 500 ml of ®Dowtherm (mixture of 26.5% by weight of diphenyl and 73.5% by weight of diphenyl ether) in the presence of glass beads. The glass beads are then separated and washed with 500 ml of ®Dowtherm. The resultant suspension is heated to 90° C. and 232 g (2.35 mol) of benzonitrile are added dropwise over 1 hour such that the temperature does not rise above 105° C. Sniffing is continued for 3 hours at 95° C., then the reaction mixture is cooled to 15° C. and 260.4 g (2.4 mol) of ethyl chloroformate are added dropwise over 2 hours. The reaction mixture is then heated to 170° C. and the pressure is lowered to 150–80 mbar, whereupon 300 g of distillate consisting of ethanol, urethane and ®Dowtherm are distilled over. After a reaction time of 2 hours, the batch is cooled, filtered, and the filter residue is washed with 1 liter of methanol, giving 255.4 g of a white product of formula

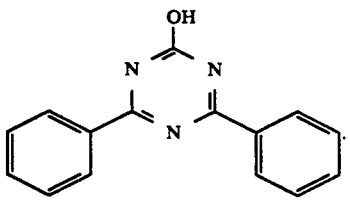

(101)

Yield: 90.2% of theory
mp 296°–297° C.

EXAMPLES 2 TO 5

The procedure of Example 1 is repeated, except that 2.35. mol of benzonitrile are replaced in each case by 2.35 mol of the substituted benzonitriles listed in Table 1.

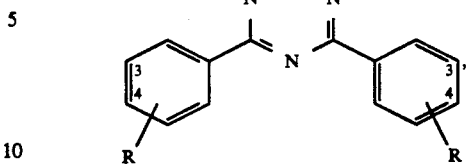

(1)

which comprises reacting an aromatic nitrile with an alkyl haloformate and an alkali metal amide, using an equimolar amount of each, in accordance with the reaction scheme

| Benzonitrile | Final product | Compound No. |
|---|---|---|
| H₃C—⟨⟩—CN | (structure with two p-tolyl groups) | (102) |
| CH₃-⟨⟩-CN | (structure with two m-tolyl groups) | (103) |
| Cl—⟨⟩—CN | (structure with two p-chlorophenyl groups) | (104) |
| Cl-⟨⟩-CN | (structure with two m-chlorophenyl groups) | (105) |

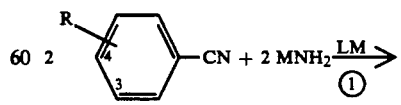

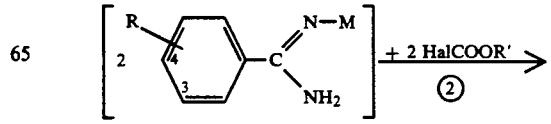

The 2-hydroxy-4,6-diaryl-1,3,5-triazines of formulae (102) to (105) are obtained in comparable yields.

What is claimed is:

1. A process for the preparation of a 2-hydroxy-4,6-diaryl-1,3,5-triazine of formula -continued

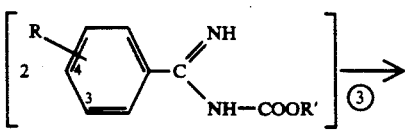

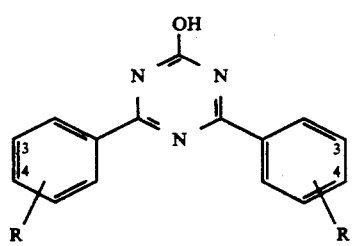

wherein

R is hydrogen, chlorine or methyl bound to phenyl in the 3- or 4-position,

R' is $C_1$–$C_4$alkyl

Hal is a halogen atom,

M is an alkali metal, and

LM is an inert organic solvent having a boiling point in the range from 160° to 250° C.

2. A process according to claim 1, wherein the alkali metal amide is sodium amide.

3. A process according to claim 1, wherein the aromatic nitrile is benzontrile.

4. A process according to claim 1, wherein the alkyl haloformate is an alkyl chloroformate.

5. A process according to claim 1, wherein the inert organic solvent is selected from the group consisting of o-dichlorobenzene, nitrobenzene, 1,2,3-trimethylbenzene, a mixture of 26.5% by weight of diphenyl and 73.5% by weight of diphenyl ether and anisole.

6. A process according to claim 5, wherein the solvent is a mixture of 26.5% by weight of diphenyl and 73.5% by weight of diphenyl ether.

7. A process according to claim 1, wherein the reaction of the first step is carried out in the temperature range from 50° to 150° C., the reaction of the second step from 5° to 50° C., and the reaction of the third step in the range from 120° to 230° C.

8. A process according to claim 1, wherein the cyclisation of step 3 is carried out under reduced pressure in the range from 50 to 200 mbar.

* * * * *